United States Patent
Evans et al.

(10) Patent No.: US 7,371,241 B2
(45) Date of Patent: May 13, 2008

(54) MULTI-USE SURGICAL CEMENT DISPENSER APPARATUS AND KIT FOR SAME

(75) Inventors: Avery J. Evans, Tampa, FL (US); Mike Plishka, Northbrook, IL (US); Michael A. Morris, Indianapolis, IN (US)

(73) Assignee: Modmed Therapeutics, Inc., Tampa, FL (US)

( * ) Notice: Subject to any disclaimer, the term of this patent is extended or adjusted under 35 U.S.C. 154(b) by 0 days.

(21) Appl. No.: 10/074,959

(22) Filed: Feb. 12, 2002

(65) Prior Publication Data
US 2004/0204715 A1    Oct. 14, 2004

Related U.S. Application Data

(60) Provisional application No. 60/267,717, filed on Feb. 12, 2001.

(51) Int. Cl.
*A61B 17/58* (2006.01)
*A61F 2/00* (2006.01)

(52) U.S. Cl. .................................... 606/92

(58) Field of Classification Search ............... 604/134, 604/135, 152, 154, 155, 218, 224, 208, 209, 604/210, 211, 228, 97.01, 97.02, 97.03, 187, 604/188, 189, 227; 433/89, 90; 606/92, 606/93, 94
See application file for complete search history.

(56) References Cited

U.S. PATENT DOCUMENTS

| | | | |
|---|---|---|---|
| 3,281,023 A * | 10/1966 | Bruck et al. ............... 222/390 |
| 3,754,687 A | 8/1973 | Norton ........................ 222/309 |
| 4,253,589 A | 3/1981 | Kiste, Jr. ..................... 222/390 |
| 4,312,343 A | 1/1982 | LeVeen et al. .............. 128/218 |
| 4,338,925 A * | 7/1982 | Miller ........................ 606/94 |
| 4,444,560 A * | 4/1984 | Jacklich ..................... 604/224 |
| 4,498,904 A * | 2/1985 | Turner et al. ............... 604/211 |
| 4,560,352 A * | 12/1985 | Neumeister et al. .......... 433/90 |
| 4,583,974 A * | 4/1986 | Kokernak ................... 604/211 |
| 4,655,749 A | 4/1987 | Fischione ................... 604/98 |

(Continued)

*Primary Examiner*—Anuradha Ramana
(74) *Attorney, Agent, or Firm*—Kelley Drye & Warren LLP

(57) ABSTRACT

The present invention is directed to a system and method for percutaneous delivery of bone cement during a surgical procedure. The system of the present invention has a plunger assembly 100, comprising: a shaft having a first end, a middle section, and a second end, wherein the middle section is threaded; and a handle attached to the first end of the shaft. The system further comprises a dispenser hub assembly 200 around the shaft having a collar and a handgrip attached to the collar, and a threaded portion formed on an interior surface of the collar. The system may further comprise a hollow tube 300 for containing the bone cement during the surgical procedure having a first end and a second end, the first end of the hollow tube adapted to be removably engaged with the threaded portion of the dispenser hub assembly. The shaft is axially displaceable through the hollow tube for controlled displacement of the bone cement through the second end of the hollow tube. The system of the present invention may be provided as a kit, which may further comprise: at least one tubing assembly, at least one cannula, and at least one stylet. The stylet may have a tip geometry selected from the group consisting of: a sharp pyramid tip, an angled tip, a blunt tip, and a corkscrew tip.

7 Claims, 8 Drawing Sheets

U.S. PATENT DOCUMENTS

| | | | |
|---|---|---|---|
| 4,671,263 A * | 6/1987 | Draenert | 606/94 |
| 4,710,179 A | 12/1987 | Haber et al. | 604/211 |
| 4,738,664 A * | 4/1988 | Prindle | 604/228 |
| 4,832,692 A * | 5/1989 | Box et al. | 604/99.01 |
| 4,994,065 A | 2/1991 | Gibbs et al. | 606/92 |
| 5,041,120 A | 8/1991 | McColl et al. | 606/99 |
| 5,156,606 A * | 10/1992 | Chin | 606/86 |
| 5,207,357 A | 5/1993 | Aronie et al. | 222/134 |
| 5,242,082 A | 9/1993 | Giannuzzi | 222/82 |
| 5,254,086 A | 10/1993 | Palmer et al. | 604/38 |
| 5,290,260 A | 3/1994 | Stines | 604/224 |
| 5,341,958 A | 8/1994 | Bayat et al. | 222/63 |
| 5,401,246 A * | 3/1995 | Mazur et al. | 604/110 |
| 5,409,465 A | 4/1995 | Boggs et al. | 604/191 |
| 5,431,654 A | 7/1995 | Nic | 606/92 |
| 5,586,821 A * | 12/1996 | Bonitati et al. | 366/139 |
| 5,603,701 A | 2/1997 | Fischer | 604/211 |
| 5,728,075 A | 3/1998 | Levander | 604/211 |
| 5,762,239 A | 6/1998 | Cossette | 222/326 |
| 5,797,899 A | 8/1998 | Tilton, Jr. | 606/1 |
| 5,839,612 A | 11/1998 | Burke | 222/333 |
| 5,893,488 A | 4/1999 | Hoag et al. | 222/391 |
| 5,951,160 A | 9/1999 | Ronk | 366/130 |
| 6,019,765 A | 2/2000 | Thornhill et al. | 606/94 |
| 6,019,776 A | 2/2000 | Preissman et al. | 606/185 |
| 6,033,411 A | 3/2000 | Preissman | 606/99 |
| 6,116,773 A | 9/2000 | Murray | 366/139 |
| 6,156,045 A | 12/2000 | Ulbrich et al. | 606/151 |
| 6,352,585 B1 * | 3/2002 | Diesso | 106/35 |
| 6,383,190 B1 * | 5/2002 | Preissman | 606/94 |
| 6,395,007 B1 * | 5/2002 | Bhatnagar et al. | 606/94 |
| 6,736,537 B2 * | 5/2004 | Coffeen et al. | 366/130 |
| 6,749,595 B1 * | 6/2004 | Murphy | 604/500 |
| 6,783,515 B1 * | 8/2004 | Miller et al. | 604/224 |

* cited by examiner

MULTI-USE SURGICAL CEMENT DISPENSER APPARATUS AND KIT FOR SAME

CROSS REFERENCE TO RELATED PATENT APPLICATION

This application claims priority on U.S. Provisional Patent Application Ser. No. 60/267,717, for Multi-use Surgical Cement Dispenser and Kit for Same, filed Feb. 12, 2001.

FIELD OF THE INVENTION

The present invention relates to a system and method for administering cement to locations within a patient. More specifically, the invention relates to a multi-use surgical cement dispenser apparatus and kit for the percutaneous delivery of bone cement.

BACKGROUND OF THE INVENTION

As the population ages, cases of bone fracture and skeletal fragility, such as those caused by osteoporosis, have become more prevalent. The development of medical procedures to combat these problems has become increasingly vital. One procedure to prevent progressive bone loss and structural weakness in patients with bone fractures is the injection of bone cement (or cement-like material) into the damaged area. The procedure is performed to reinforce the fractured bone, prevent further damage, and alleviate pain associated with the injury.

The cement delivery process is a percutaneous procedure performed by highly skilled medical personnel. Using X-ray, fluoroscopic guidance, or other imaging techniques, the physician positions a needle through the patient's skin and into the affected area. After other equipment, including a cement delivery apparatus, is attached to the needle, medical grade cement is injected into the patient. The cement is injected in a liquid form that quickly hardens to reinforce the damaged area. The procedure can often provide pain relief and increased mobility for the patient within only a few days.

The medical personnel who work to treat bone fractures, however, are faced with significant challenges. Conventional devices used to deliver the bone cement to the patient are complex, costly, and difficult to use. Simpler devices are often less effective in delivering the bone cement to the patient, leading to longer and more traumatic surgical procedures for the patient. Still other devices are difficult to clean and maintain, and cannot be used for multiple procedures, leading to greater expense for the medical provider, and consequently, the patient.

Moreover, the kits in which cement dispenser devices are provided to medical personnel are often inadequately and inefficiently designed. Kit products on the market for bone cement delivery today typically allow the user up to two cement dispensers per kit. If the physician takes on a procedure that requires more than two injections of cement, they must either try to clean out a device that they just used, or open up another kit. Given the high cost of each kit, the procedure becomes expensive if more than one kit is used. Moreover, the cement that is used for these procedures begins to harden after about 20 minutes, making it quite difficult to clean up a device for multiple uses. Therefore, what is needed is an apparatus and kit that provides medical personnel with a safe, effective, affordable, flexible, and convenient system for the percutaneous delivery of bone cement.

BACKGROUND ART

U.S. Pat. No. 6,019,765 to Thornhill et al. is directed to a morsellized bone allograft applicator device. Thornhill does not disclose, however, a simple, multi-use surgical cement dispenser and kit having a funnel shaped opening built into disposable hollow tubes. U.S. Pat. No. 5,603,701 is directed to a syringe apparatus with a threaded plunger for delivering tooth composites. The '701 patent does not disclose, however, a simple, multi-use surgical cement dispenser and kit adapted to deliver bone cement to a patient during a surgical procedure.

Moreover, U.S. Pat. No. 5,431,654 relates to a bone cement injector having an intricate delivery mechanism and U.S. Pat. No. 5,893,488 is directed to a bone cement injector gun for dispensing bone cement from a cartridge using a trigger assembly. Neither the '654 patent nor the '488 patent discloses, however, a simple, multi-use surgical cement dispenser and kit according to the present invention.

The designs of many known systems are complex, ineffective, and costly. Thus, there remains a need for a simple system and method for providing the percutaneous delivery of bone cement to a patient.

The present invention answers this need. The cement dispenser apparatus of the present invention is designed to provide medical personnel with the ability to perform multiple cement deliveries in an effective manner, and at a minimal cost. In addition, the cement dispenser kits of the present invention provide the physician with much needed flexibility.

It is therefore an aspect of the present invention to provide physicians with a safe, effective, affordable, and convenient apparatus and kit for percutaneous delivery of bone cement.

It is another aspect of the present invention to provide a multi-use cement dispenser apparatus.

It is yet another aspect of the present invention to provide an apparatus designed to provide physicians with opportunities to perform multiple cement deliveries for a minimal cost.

One embodiment of the present invention is directed to a multi-use cement dispenser apparatus with a 10 cc size syringe.

In another embodiment of the present invention there is provided a multi-use cement dispenser apparatus with a small bore size for optimal mechanical advantage.

A more preferred embodiment of the present invention provides an ergonomically designed multi-use cement dispenser apparatus.

The present invention also provides a needle set designed specifically for bone cement delivery. The needles are provided with thinner wall thickness resulting in decreased patient trauma. The inventive device also provides stylets and tubing designed for ease of attachment to the cannulae.

In general, the present invention provides a multi-use cement dispenser apparatus which is lighter resulting in easier manipulation of the needle by the physician. The present invention also relates to at least four different styles of stylet tips. The present invention also provides a long tubing length for cement delivery.

It is still another aspect of the present invention to provide a multi-use cement dispenser apparatus and kit in modular packaging trays. This provides the physician with flexibility in ordering kits for cement delivery. The kits are designed such that the physician need only order materials that are necessary for a particular procedure. This allows the physician to avoid excess costs on components which are not needed for a particular procedure.

It is yet another aspect of the present invention to provide disposable syringes in a multi-use cement dispenser apparatus permitting the product to be inexpensive for simpler procedures, while maintaining the capability to accommodate the most complex procedures.

It is still yet another aspect of the present invention to provide a kit with multiple number of disposable syringes.

Additional aspects and advantages of the invention are set forth, in part, in the description which follows and, in part, will be apparent to one of ordinary skill in the art from the description and/or from the practice of the invention.

SUMMARY OF THE INVENTION

In response to the foregoing challenges, Applicants have developed an innovative, economical apparatus for the percutaneous delivery of bone cement. Applicants have also developed an innovative, economical kit for same.

A preferred embodiment of the present invention allows a physician to deliver cement in the liquid form to all of the necessary locations in a patient. The apparatus according to a preferred embodiment of the present invention is capable of generating the pressure required for cement delivery. The apparatus according to a preferred embodiment of the present invention may be composed of a readily cleaned material, such as, for example, plastic, and is designed to be robust enough and with features that allow it to be used multiple times on a single patient during a surgical procedure. The apparatus according to a preferred embodiment of the present invention may come as a part of a kit that includes all of the necessary components required for cement delivery, and the components may be disposed of after the surgical procedure is completed.

In one embodiment, the present invention is a system for the percutaneous delivery of bone cement during a surgical procedure. The system in a preferred embodiment has a plunger assembly, comprising: a shaft having a first end, a middle section, and a second end, wherein the middle section is threaded; and a handle attached to the first end of the shaft. The system further comprises a dispenser hub assembly formed around the shaft having a collar and a hand-grip attached to the collar, and a threaded portion formed on an interior surface of the collar. The system may further comprise a hollow tube for containing the bone cement during the surgical procedure having a first end and a second end, the first end of the hollow tube adapted to be removably engaged with the threaded portion of the dispenser hub assembly. The shaft is axially displaceable through the hollow tube for controlled displacement of the bone cement through the second end of the hollow tube.

In another embodiment, the present invention is a cement dispensing apparatus for percutaneous delivery of bone cement from a disposable hollow tube to a patient during a surgical procedure. The apparatus comprises actuation means, which comprises a shaft having a first end, a middle section, and a second end; and a handle attached to the first end of the shaft. The apparatus further comprises a dispenser hub assembly, formed around the shaft of the actuation means, the dispenser hub assembly having a collar and a hand-grip attached to the collar, and a threaded portion formed on an interior surface of the collar adapted to receive the disposable hollow tube.

In yet another embodiment, the present invention is a multi-use cement dispenser kit comprising: cement delivery means for delivering bone cement into a patient during a surgical procedure, and at least one hollow tube for containing the bone cement during the surgical procedure. The cement delivery means may comprise a plunger assembly, having a shaft and a handle attached to one end of the shaft; and a dispenser hub assembly, formed around the shaft of the plunger assembly. The hollow tube is adapted to be removably attached to the cement delivery means, wherein the shaft of the cement delivery means is axially displaceable through the hollow tube for controlled displacement of the bone cement through the hollow tube. The multi-use cement dispenser kit may further comprise: at least one tubing assembly, at least one cannula, and at least one stylet.

In still another embodiment, the present invention discloses a method for the percutaneous delivery of bone cement into a patient during a surgical procedure using a multi-use cement dispensing apparatus. The method comprises the steps of: filling a disposable hollow tube with the bone cement; attaching a first end of the hollow tube to the multi-use cement dispensing apparatus; attaching a second end of the hollow tube to a cannulae assembly inserted into the patient; applying an external rotational force to the multi-use cement dispensing apparatus for delivery of the bone cement through the hollow tube, the cannulae assembly, and into the patient; removing the hollow tube from the multi-use cement dispensing apparatus and the cannulae assembly; and repeating the above steps as necessary until the surgical procedure is completed.

It is to be understood that both the foregoing general description and the following detailed description are exemplary and explanatory only, and are not restrictive of the invention as claimed. The accompanying drawings, which are incorporated herein by reference, and which constitute a part of this specification, illustrate certain embodiments of the invention, and together with the detailed description serve to explain the principles of the present invention.

DETAILED DESCRIPTION OF THE PREFERRED EMBODIMENTS

Figure 1:
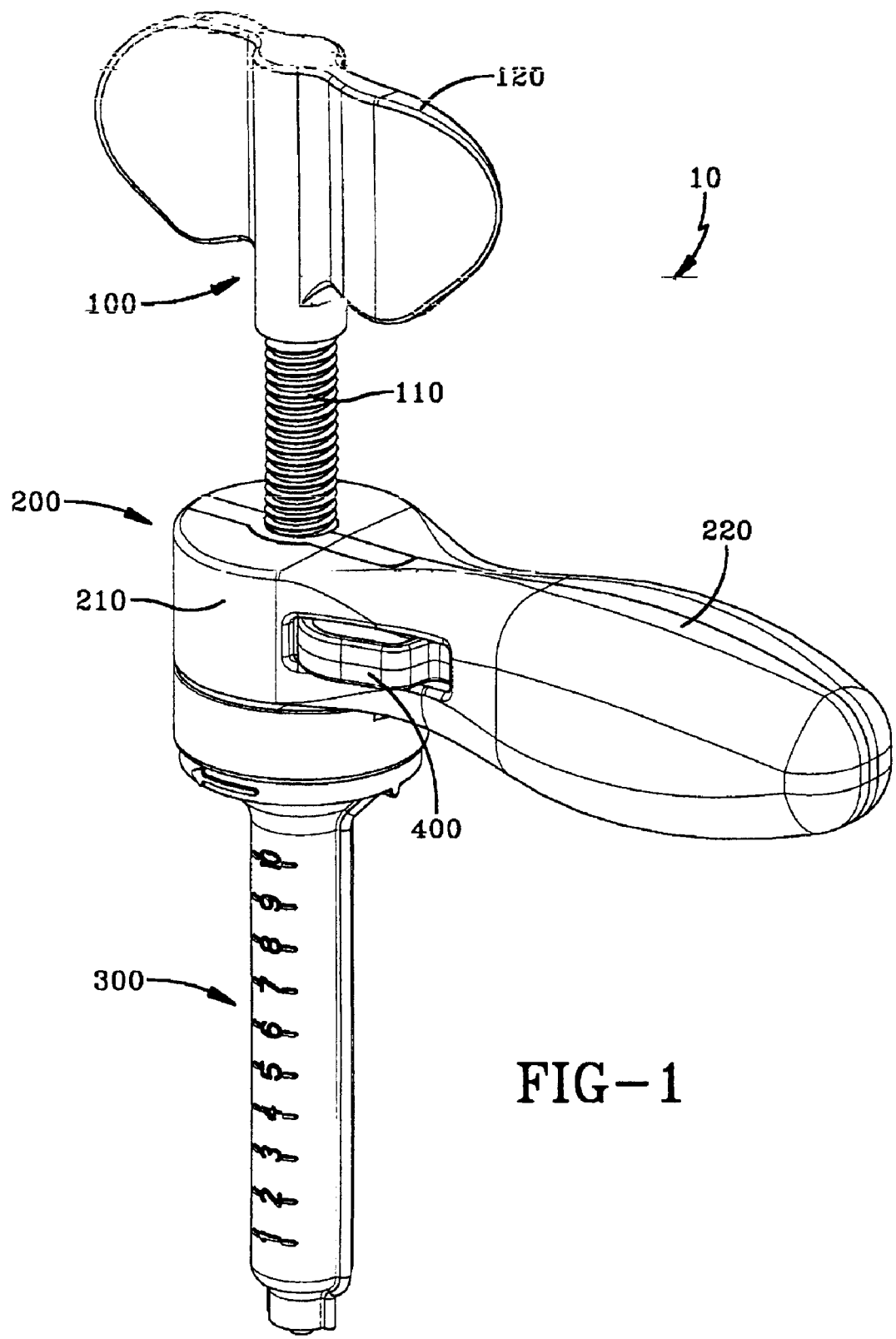
FIG. 1 is a schematic representation of the multi-use cement dispenser apparatus according to an embodiment of the present invention.

Reference will now be made in detail to a preferred embodiment of the present invention, an example of which is illustrated in the accompanying drawings. An embodiment of the cement dispenser apparatus 10 of the present invention is shown in FIG. 1. In a preferred embodiment of the present invention, the cement dispenser apparatus 10 includes a plunger assembly 100, a dispenser hub assembly 200, and a tube assembly 300 for containing the bone cement. When subjected to an external rotational force, the plunger assembly 100 is axially displaceable through the tube assembly 300 for the controlled delivery of bone cement during a surgical procedure.

Figure 2:
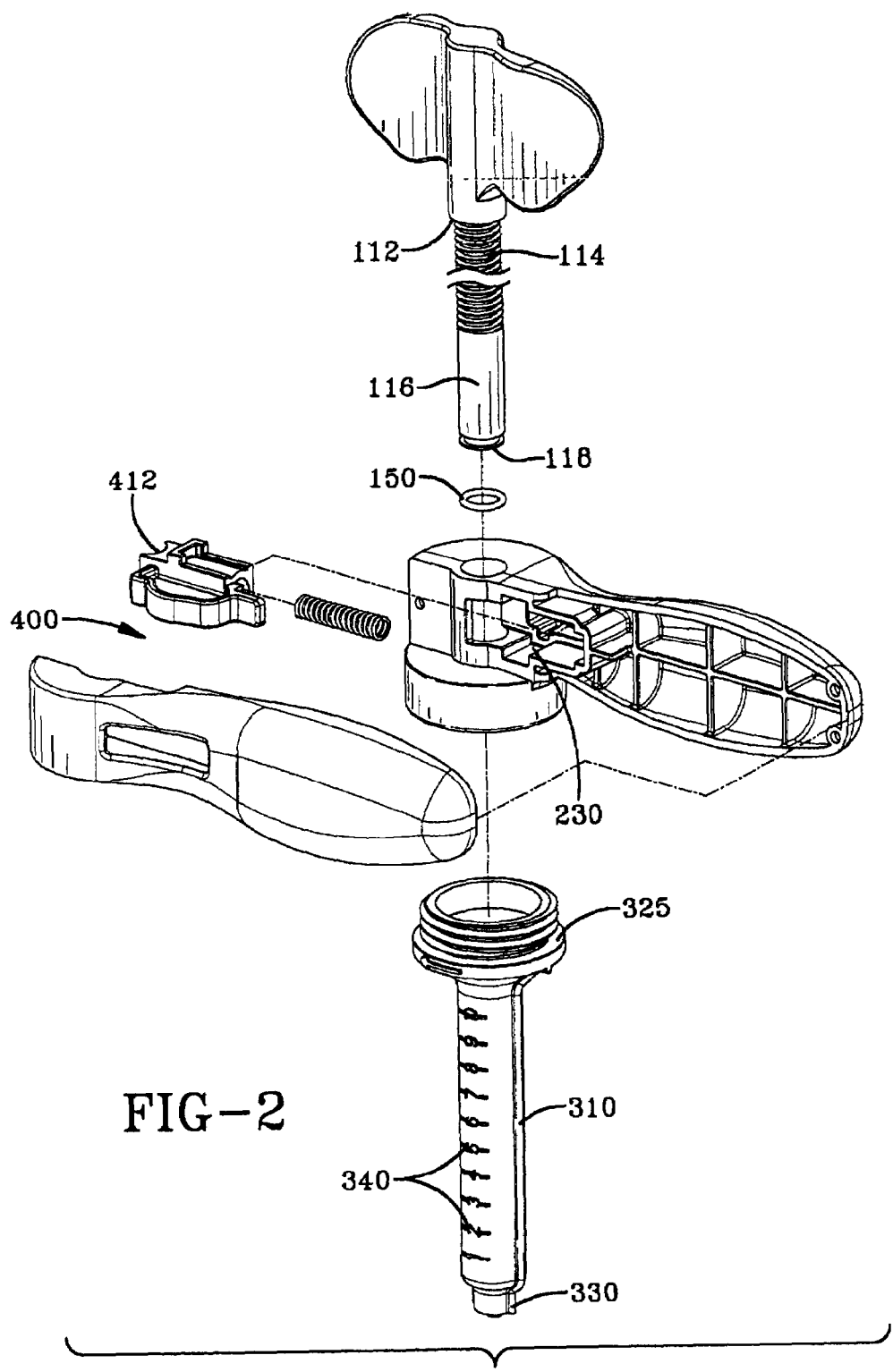
FIG. 2 is an exploded view of the multi-use cement dispenser apparatus according to an embodiment of the present invention.

In a preferred embodiment of the present invention, the plunger assembly 100 comprises a shaft 110 and a handle 120. As shown in FIG. 2, the shaft 110 includes an unthreaded upper portion 112 secured to the handle 120. The shaft 110 further includes a threaded middle portion 114 and an unthreaded lower portion 116. Because the lower portion 116 of the shaft 110 is unthreaded, the plunger assembly 100 cannot be inadvertently withdrawn beyond the starting position without use of the release assembly 400, to be discussed below.

In a preferred embodiment of the present invention, the lower portion 116 of the shaft 110 includes a groove 118 formed therein, as shown in FIG. 2. The groove 118 is adapted to receive an O-ring 150 for creating a seal between the shaft 110 of the plunger assembly 100 and an interior surface of the tube assembly 300 and facilitating the delivery of the bone cement. The O-ring 150 may be composed of Teflon or any other suitable material. Other means for creating a seal between the shaft 110 and an interior surface of the tube assembly 300 are considered well within the scope of the present invention.

According to one embodiment of the present invention, the plunger assembly 100 may be composed of a readily cleanable material, such as, for example, plastic, or any other suitable material. The handle 120 of the plunger assembly 100 is preferably contoured for the comfort of the user. In one embodiment, the shaft 110 of the plunger assembly 100 is approximately 180 mm long, having a diameter of approximately 12.4 mm. The shaft 110 is preferably cored out with a wall thickness of approximately 2.5 mm typical throughout the part. Other lengths, diameters, and thicknesses of the shaft 110 that are adapted to provide the user with control of the cement injection are considered well within the scope of the present invention.

Figure 5:
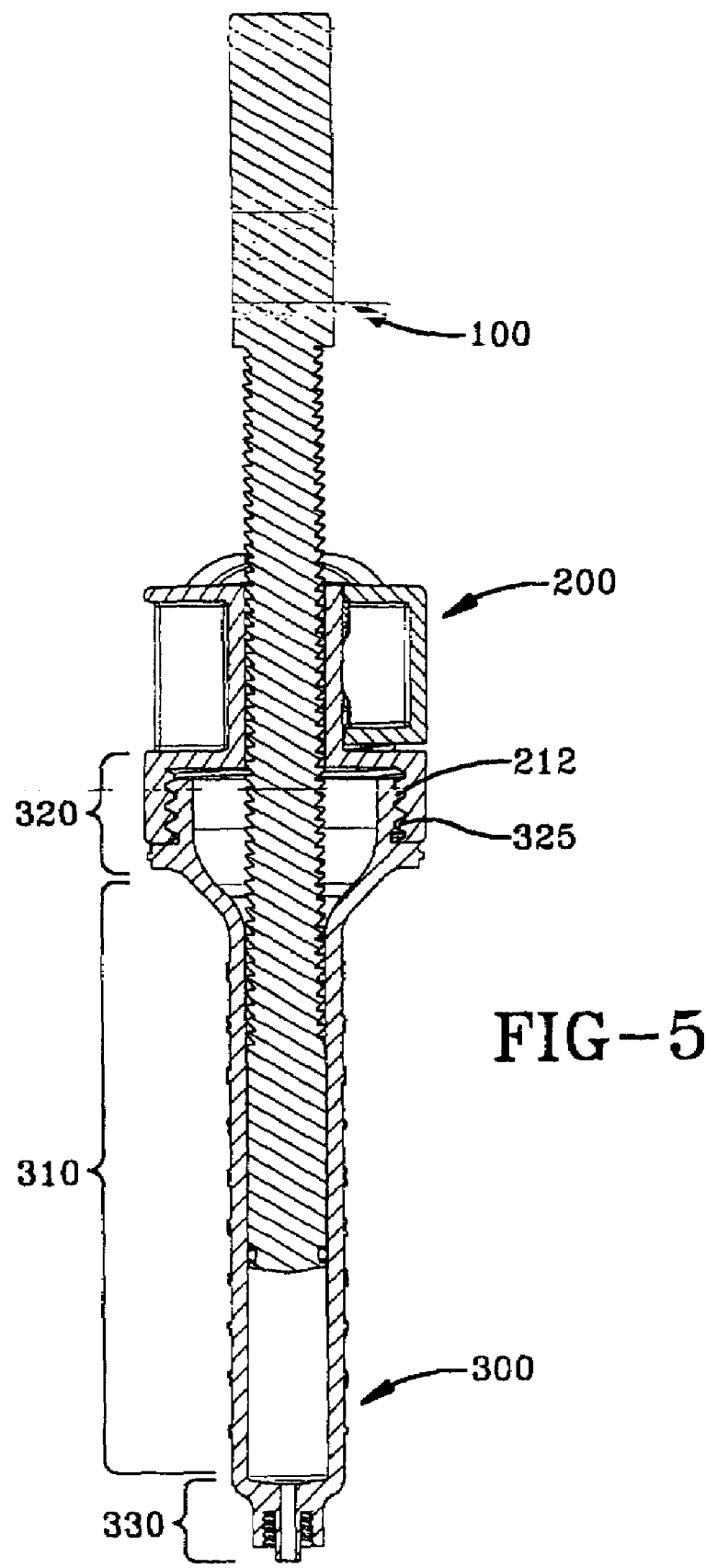
FIG. 5 is a cross-sectional view of the multi-use cement dispenser apparatus shown in FIG. 3 along section lines 5-5.

In a preferred embodiment of the present invention, the dispenser hub assembly 200 comprises a collar 210 formed around the shaft 110, and a hand-grip 220 attached to the collar 210. The hand-grip 220 is preferably contoured for the comfort of the user. As shown in FIG. 5, an interior surface of the collar 210 includes a threaded portion 212 formed thereon for removably engaging the tube assembly 300. In one embodiment of the present invention, the threaded portion 212 does not extend all the way to the opening of the dispenser hub assembly 200. The resulting unthreaded portion helps the user guide the tube assembly 300 into the opening of the collar 210 of the dispenser hub assembly 200 prior to attaching the tube assembly 300 to the dispenser hub assembly 200.

In one embodiment of the present invention, as shown in FIG. 2, the dispenser hub assembly 200 further includes a void 230 adapted to receive the release assembly 400, to be discussed below.

The dispenser hub assembly 200 may be composed of plastic or any other suitable material. In one embodiment of the present invention, the dispenser hub assembly 200 is manufactured in two halves that are welded together ultrasonically, or by any other suitable means, around the plunger assembly 100. Other methods for manufacturing the dispenser hub assembly 200 are considered well within the skill of the ordinary artisan and the scope of the present invention.

Figure 3:
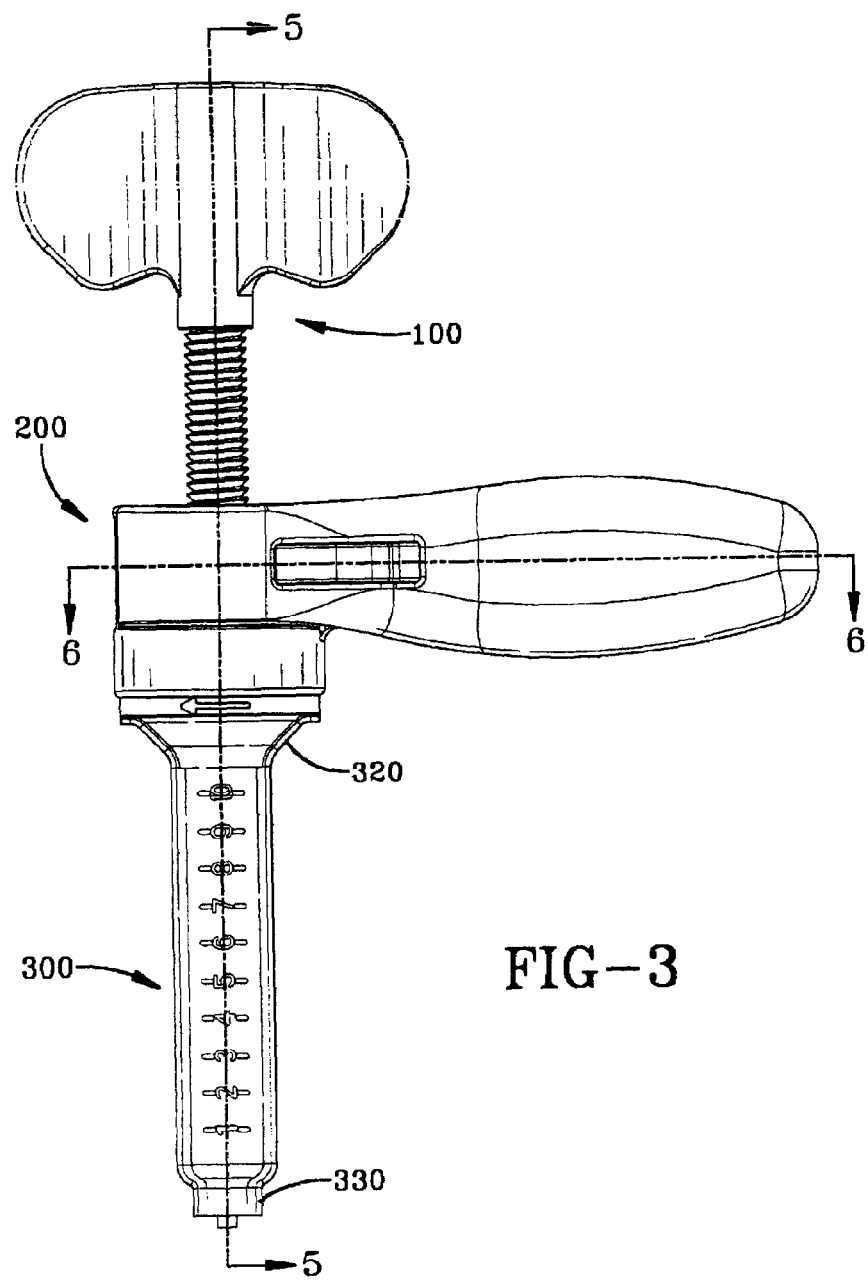
FIG. 3 is a side view of the multi-use cement dispenser apparatus according to an embodiment of the present invention.
Figure 4:
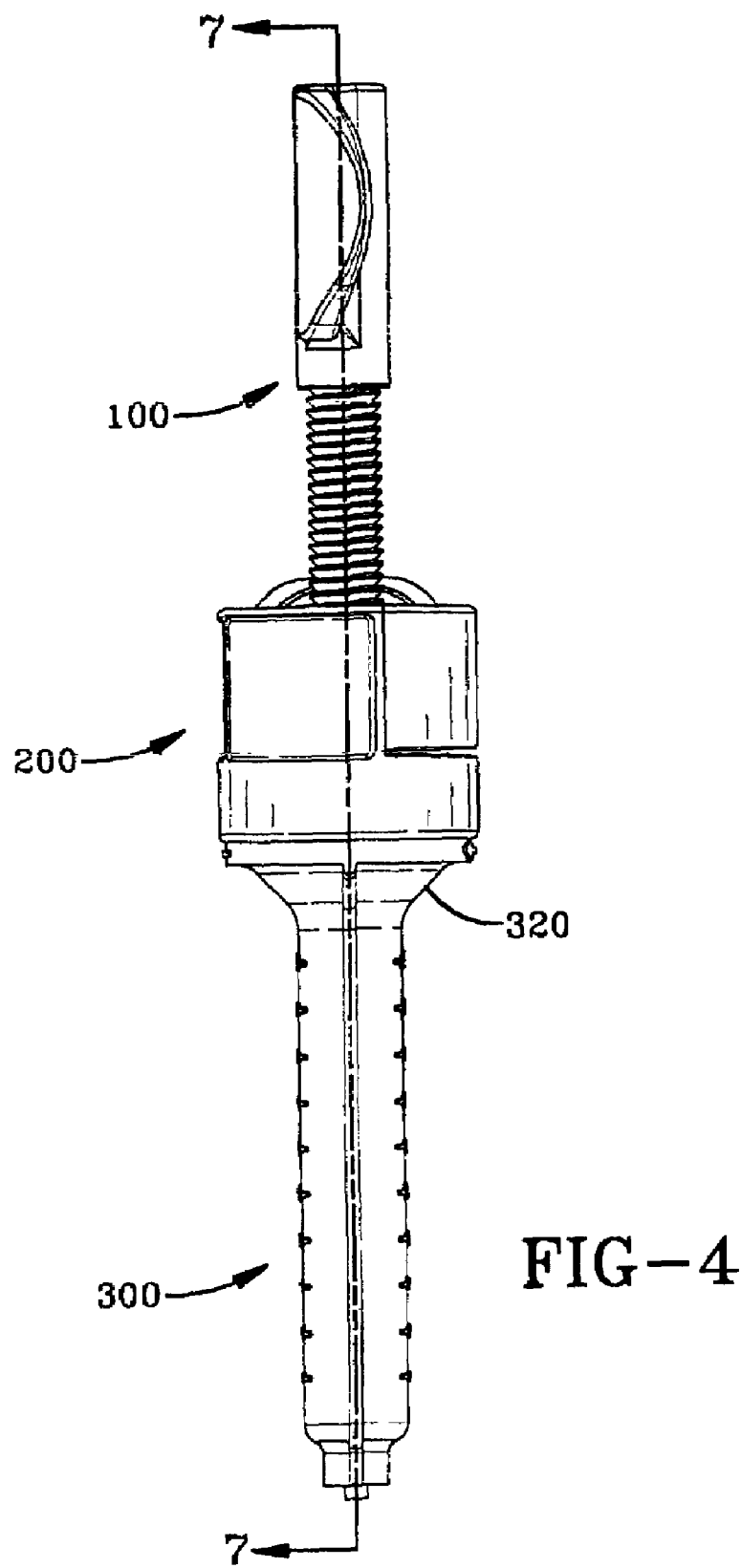
FIG. 4 is a top view of the multi-use cement dispenser apparatus according to an embodiment of the present invention.

In the preferred embodiment of the present invention, the tube assembly 300 includes a hollow tube member 310. The hollow tube member 310 is adapted to hold bone cement for use during a surgical procedure. At a first end, the tube assembly 300 has a funnel-shaped opening 320, as shown in FIGS. 3 and 4, that facilitates receipt of bone cement into the tube assembly 300. Other embodiments of the opening 320 for facilitating receipt of the bone cement are considered well within the scope of the present invention. A second end 330 of the tube assembly 300 has an opening through which the bone cement is delivered and is adapted to receive a tubing assembly (not shown), to be discussed below, for use in a surgical procedure in which bone cement is delivered to the patient.

As shown in FIG. 2, the tube assembly 300 further includes a threaded portion 325 for removably engaging the threaded portion 212 of the collar 210. After the cement has been dispensed from the tube assembly 300, it may be removed and discarded. In this manner, the tube assembly 300 is disposable.

The tube assembly 300 may be composed of plastic or any other suitable material. The hollow tube member 310 is approximately 89 mm long with an inner diameter of approximately 13 mm. The inner diameter of the opening 320 is approximately 30 mm. The tube member 310 preferably holds a total of approximately 10 cc of bone cement, which is an appropriate amount for the types of procedures that use the present invention. Other suitable sizes for the opening 320 and the tube member 310, however, are considered well within the skill of the ordinary artisan and the scope of the present invention.

In a preferred embodiment, a plurality of graduation markings 340 are located on an exterior surface of the tube member 310, as shown in FIG. 2. The graduation markings are preferably spaced in 1 cc increments. In a preferred embodiment of the present invention, the material used for the tube assembly 300 is transparent in order for the user to witness the amount of cement dispensed.

Figure 6:
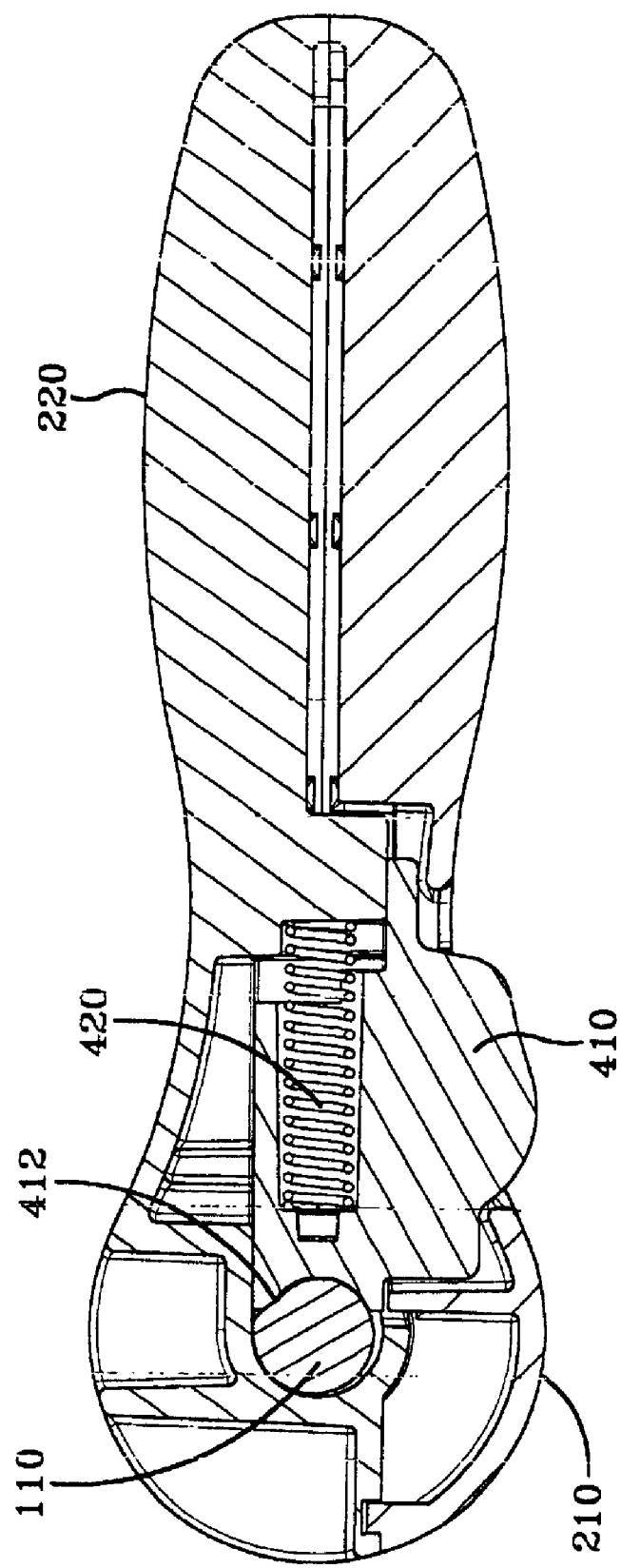
FIG. 6 is a cross-sectional view of the multi-use cement dispenser apparatus shown in FIG. 3 along section lines 6-6.

In one embodiment of the present invention, the dispenser hub assembly 200 further includes the release assembly 400 for controlling the axial displacement of the shaft 110. The release assembly 400 is disposed in the void 230 of the dispenser hub assembly 200. The release assembly 400 includes a trigger 410 and a spring 420 having a first end in contact with the trigger 410 and a second end in contact with the dispenser hub assembly 200, as shown in FIG. 6. The trigger includes a recess 412, or other contact surface, adapted to contact the shape of the shaft 110. The spring 420 is biased such that the recess 412 is forced against the shaft 110.

Figure 7:
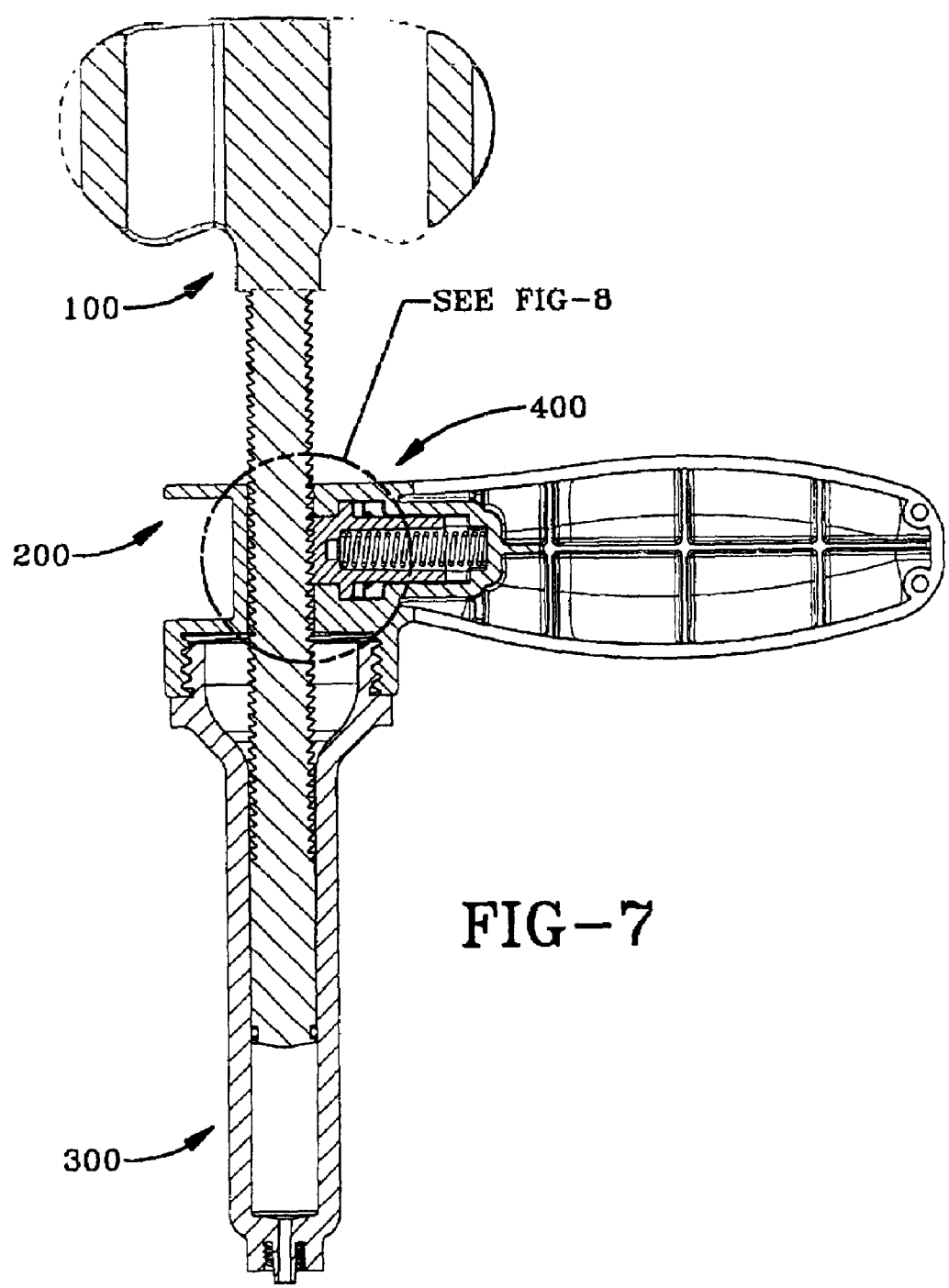
FIG. 7 is a cross-sectional view of the multi-use cement dispenser apparatus shown in FIG. 4 along section lines 7-7.
Figure 8:
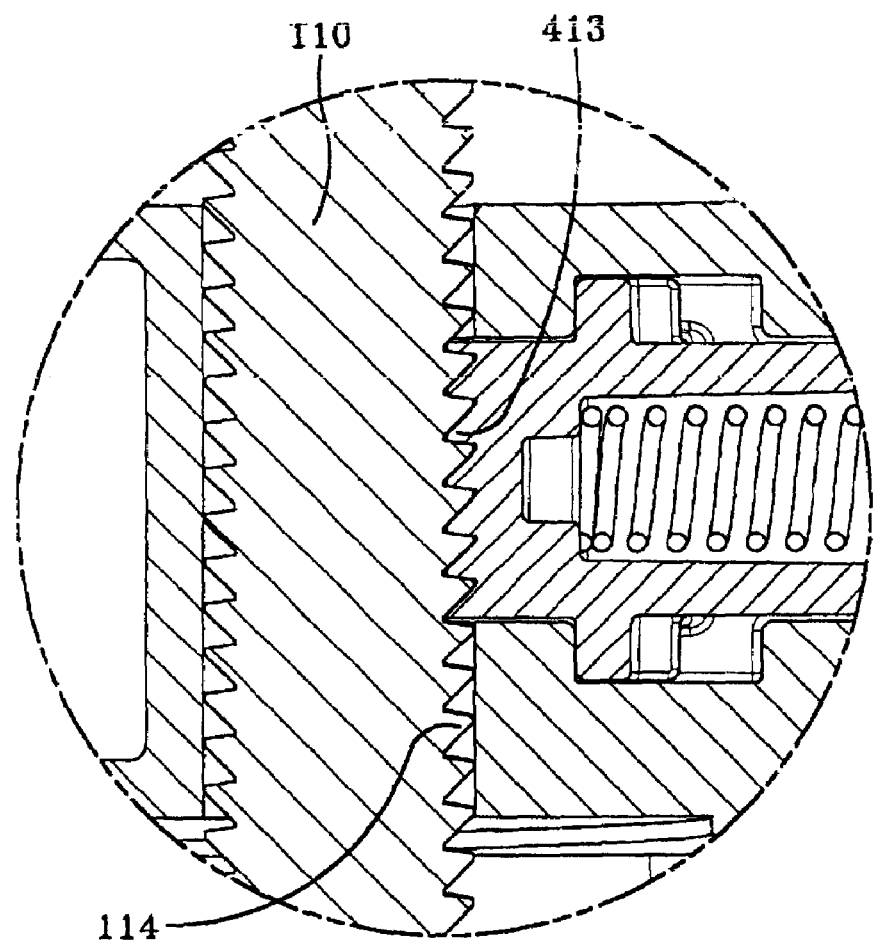
FIG. 8 is an enlarged view of the release assembly shown in FIG. 7 according to an embodiment of the present invention.

As shown in FIGS. 7 and 8, the recess 412 includes a threaded portion 413 that releasably engages the threaded middle portion 114 of the shaft 110, allowing the shaft 110 to be advanced into and through the tube member 310. The threaded portion 413 of the recess 412 is biased so as to withstand pressure exerted from the bone cement in the tube member 310, yet adapted to ease the insertion and advancement of the shaft 110 through the recess 412. The threaded portion preferably comprises American National Standard buttress inch screw threads (ANSI B1.9-1973), however, other designs are considered well within the skill of the ordinary artisan and the scope of the present invention.

When the user applies a force to the trigger 410 sufficient to overcome the bias force of the spring 420, the threaded portion 413 of the recess 412 disengages the shaft 110. When the recess 412 is disengaged from the threaded middle portion 114, the shaft 110 may be withdrawn expeditiously from the tube assembly 300. In addition, the release assembly 400 may be used to release pressure that may occur while applying bone cement to a patient during a surgical procedure. When the recess 412 is disengaged from the threaded middle portion 114, any excess pressure is free to displace the shaft 110 in the upward direction in the tube member 310.

Multi-use Surgical Cement Dispenser Kit of the Present Invention

In a preferred embodiment of the present invention, a cement dispenser kit includes: a plunger assembly, a dispenser hub assembly, at least one tube assembly, at least one tubing assembly, at least one stylet, and at least one cannula.

In a more preferred embodiment of the present invention, the cement dispenser kit includes from one (1) to eight (8) tube assemblies, depending on the quantity the user feels will be needed to complete the surgical procedure. It is contemplated by the present inventors, however, that any suitable number of tube assemblies may be provided in the cement dispenser kit. In one embodiment, the tube assemblies are provided in the cement dispenser kit empty. In another embodiment, the tube assemblies are pre-filled with medical grade bone cement, or other suitable material, in a manner such that the cement is not susceptible to undesirable hardening prior to use.

The tubing assembly has a first end adapted to secure to the second end 330 of the tube assembly 300, and a second end adapted to secure to the cannula. The tubing assembly preferably includes a luer fitting at each end to facilitate securing to the second end 330 of the tube assembly 300 and the cannula. In one embodiment, a rotatable luer fitting is used to secure the tubing assembly to the tube assembly 300, which provides an additional degree of freedom to the physician. The tubing assembly may be made out of PEEK (polyethertherketone), or any other suitable material, and the length is adapted such that the user is at a safe distance from the fluoroscopic imaging instruments that may be in use during the procedure. In one embodiment, the tubing assembly is approximately 50 cm long. The tubing assembly 30 has an outer diameter of approximately 1/8" (approximately 3.2 mm) with an inner diameter of approximately 0.080" (approximately 2.0 mm). In the preferred embodiment, the number of tubing assemblies supplied in the cement dispenser kit is equivalent to the number of tube assemblies 300 ordered for that particular kit. In one embodiment, the tubing assembly includes a right angle bend that removes stress from the cannula during cement delivery.

The at least one stylet is inserted in the cannula. The stylet includes a tip with a geometry designed for a specific purpose. The geometry of the tip of the stylet may include, but is not limited to, a sharp pyramid tip for entry into the bone, an angled tip for redirection once in the bone, a blunt tip for safe movement through the bone, and a corkscrew tip for bone biopsy and removing hardened cement from the cannula. In a preferred embodiment of the present invention, the cement dispenser kit includes four stylets, one each of the above described stylet tip geometries. Other tip geometries for the stylet are considered to be well within the scope of the present invention. The stylet may be composed of stainless steel, or any other suitable material. The stylet has a diameter of approximately 0.086" (approximately 2.2 mm) and a length of approximately 4.85" (approximately 12.3 cm).

The cannula may be composed of stainless steel, or any other suitable material. In one embodiment, the cannula comprises 12-gauge thin-wall tubing, having an outer diameter of approximately 0.109" (approximately 2.8 mm) and an inner diameter of approximately 0.091" (approximately 2.3 mm), and a usable length of approximately 12 cm. The cannula has a hub for the attachment of both the stylet and the tubing assembly. In the preferred embodiment, the number of cannulae supplied in the cement dispenser kit is equivalent to the number of tube assemblies 300 ordered for that particular kit.

In one embodiment of the present invention, the cement dispenser kit further comprises a hammer. The hammer aids the user in installing the cannula into the bone of the patient. The hammer may be composed of stainless steel, or any other suitable material.

In another embodiment of the present invention, the cement dispenser kit further comprises a set of forceps. The forceps may be used to aid in holding the cannula while inserting it into the bone and preventing the physician from entering the radiation field that is created by the imaging tools used during the procedure. The forceps may be composed of stainless steel, or any other suitable material.

In another embodiment of the present invention, the cement dispenser kit further comprises the items commonly used to prepare a patient and the equipment for minimally invasive procedures. The preparatory items include, but are not limited to, local anesthetics, needles, saline, swabs, bandages, mixing equipment and drapes.

Other configurations and contents of the cement dispenser kit suitable for effective use during the surgical procedure are considered to be well within the scope of the present invention.

OPERATION OF THE PRESENT INVENTION

The operation of the cement dispenser apparatus 10 and the cement dispenser kit of the present invention will now be described.

As will be apparent to those of ordinary skill in the art, the patient and the damaged area is prepared for the procedure. Using X-ray, fluoroscopic guidance, or other imaging technique, the assembly of the stylet and the cannula is placed into the damaged bone of the patient. The geometry of the stylet may be selected as necessary to direct the assembly to the desired location. The stylet is then removed from the patient and the cannula may be filled with a sterile solution, such as, for example, saline.

After the cannula has been inserted into the bone of the patient, the tube assembly 300, separated from the dispenser hub assembly 200, is filled with bone cement, or other suitable material. The filling of the tube assembly 300 is facilitated by the funnel-shaped opening 320. As discussed above, the tube assembly 300 may be provided pre-filled with bone cement. In either embodiment, the tube assembly 300 holds the cement while the cement dispenser apparatus 10 is in use and provides the opening through which the cement is dispensed.

The tube assembly 300 is then secured to the dispenser hub assembly 200, which includes the plunger assembly 100 positioned therethrough, by engaging the threaded portion 325 of the tube assembly 300 with the threaded portion 212 of the dispenser hub assembly 200. The plunger assembly 100 may be advanced to purge any air that may remain in the tube assembly 300.

Once the tube assembly 300 is filled with cement and attached to the dispenser hub assembly 200, the first end of the tubing assembly is then attached to the second end 330 of the tube assembly 300. The plunger assembly 100 is then advanced slightly to prime the tubing assembly, and the second end of the tubing assembly is attached to the cannula, which has been placed in the patient. As will be apparent to those of ordinary skill in the art, the attachments are preferably made with standard quick connect luer fittings.

Gripping the hand-grip 220 with one hand, the user then rotates the handle 120 with the other, causing the shaft 110 to advance down the interior of the tube assembly 300. The advancement of the shaft 110 forces the cement out through the opening in the second end 330 of the tube assembly 300, through the tubing assembly, the cannula, and into the patient. As the shaft 110 advances, the O-ring 150 creates a seal between the shaft 110 and the interior wall of the tube member 310, facilitating the delivery of the bone cement.

If during delivery of the cement to the patient the user determines that the patient is experiencing discomfort due to excess pressure or that excess pressure is otherwise adversely affecting the surgical procedure, the user may actuate the release assembly 400 by applying a force to the trigger 410. This causes the threaded portion of the recess 412 to disengage the threaded middle portion 114 of the shaft 110. Because the shaft 110 is now free to move in the axial direction within tube assembly 300 and the dispenser hub assembly 200, the excess pressure is relieved by causing the shaft 110 to withdraw a slight amount, for example, 1 mm.

Once the tube assembly 300 is depleted of cement, or once the user has completed the delivery of cement to a particular location in a patient, the user returns the plunger assembly 100 to the starting position. This is accomplished by actuating the release assembly 400, causing the threaded portion of the recess 412 to disengage the threaded middle portion 114 of the shaft 110, and withdrawing the shaft 110 from the tube assembly 300 by pulling the plunger assembly 100 in an outward axial direction. Alternatively, the user may simply withdraw the shaft 110 by rotating the plunger assembly 100 in the direction opposite that used to advance the shaft 110 through the tube assembly 300.

After the tube assembly 300 has been withdrawn, the user may disengage the threaded portion 325 of the tube assembly 300 from the threaded portion 212 of the dispenser hub assembly 200, and remove and dispose of the tube assembly 300. If additional cement is required in the same location, the user may then prepare another tube assembly 300 from the cement dispenser kit by loading the tube member 310 with cement, and begin delivery of the cement through the same cannula, as discussed above. Alternatively, if a bipedicular approach is required, a stylet and cannula may be placed into the patient at the next location, and the above described procedure may be repeated.

The operation of the present invention may continue until the physician is satisfied that the surgical procedure has been completed. At this point, the plunger assembly 100 and the dispenser hub assembly 200 of the present invention may be discarded.

INDUSTRIAL APPLICABILITY

The medical community is constantly searching for improved procedures, equipment and kits that allow them to deliver the best medical treatment to patients in a cost effective and efficient manner. The system and method for percutaneous delivery of bone cement according to the present invention meets these needs.

It will be apparent to those skilled in the art that various modifications and variations can be made in the construction, configuration, and/or operation of the present invention without departing from the scope or spirit of the invention. For example, in the embodiments mentioned above, various changes may be made to the threaded plunger assembly and the dispenser hub assembly without departing from the scope and spirit of the invention. In addition, it is contemplated that the cement dispenser apparatus of the present invention may be provided without the tube assembly. Further, it may be appropriate to make additional modifications or changes to the tubing assembly, the cannulae, or the stylets, as well as the kits, without departing from the scope of the invention. Thus, it is intended that the present invention cover the modifications and variations of the invention provided they come within the scope of the appended claims and their equivalents.

We claim:

1. A system for percutaneous delivery of bone cement during a surgical procedure, comprising:
   a plunger assembly, comprising:
   a shaft having a first end, a middle section, and a second end, wherein said middle section is threaded; and
   a handle attached to said first end of said shaft;
   a dispenser hub assembly around said shaft, said dispenser hub assembly having a collar and a hand-grip attached to said collar, and a threaded portion formed on an interior surface of said collar;
   a hollow tube pre-filled with the bone cement for use during the surgical procedure having a first end and a second end, said first end of said hollow tube adapted to be removably engaged with said dispenser hub assembly,
   wherein said shaft is axially displaceable through said hollow tube for controlled displacement of the bone cement through said second end of said hollow tube; and
   a release assembly disposed in a void formed in said dispenser hub assembly for controlling the axial displacement of said shaft through said hollow tube.

2. The system of claim 1, said release assembly further comprising:
   a trigger having a threaded portion for releasably engaging said shaft; and
   a spring having a first end in contact with said trigger and a second end in contact with said dispenser hub assembly, wherein the bias of said spring causes said trigger to engage said shaft.

3. The system of claim 2, wherein a force applied to said trigger sufficient to overcome the bias of said spring causes said trigger to disengage said shaft and enables said shaft to be withdrawn from said hollow tube.

4. The system of claim 1, wherein said release assembly is adapted to selectively release pressure that may occur while applying the bone cement during the surgical procedure.

5. A cement dispensing apparatus for percutaneous delivery of bone cement from a disposable hollow tube to a patient during a surgical procedure, said apparatus comprising:
   actuation means, comprising:
   a shaft having a first end, a middle section, and a second end; and a handle attached to the first end of the shaft; and a dispenser hub assembly, around the shaft of said actuation means, said dispenser hub assembly having a collar and a hand-grip attached to said collar, a said collar adapted to receive the disposable hollow tube; and a release assembly disposed in a void formed in said dispenser hub assembly for controlling the axial displacement of the shaft through the disposable hollow tube, wherein said release assembly comprises: a trigger having a threaded portion for releasably engaging said shaft; and a spring having a first end in contact with said trigger and a second end in contact with said dispenser hub assembly, wherein the bias of said spring causes said trigger to engage said shaft.

6. The apparatus of claim 5, wherein the shaft of said actuation means is axially displaceable through the disposable hollow tube for controlled displacement of the bone cement through the disposable hollow tube when the handle of said actuation means is subjected to an external rotational force.

7. The apparatus of claim 5, wherein the second end of the shaft further comprises:

a groove formed therein; and sealing means located in the groove for creating a seal between the shaft and an interior surface of the disposable hollow tube for the delivery of the bone cement.

* * * * *